United States Patent
Sander et al.

(10) Patent No.: US 8,529,064 B2
(45) Date of Patent: Sep. 10, 2013

(54) ATTACHMENT MODULE FOR A MICROSCOPE FOR OBSERVING THE FUNDUS OF THE EYE

(75) Inventors: Ulrich Sander, Rebstein (CH); Lothar Knuenz, Rankwell (AT)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 118 days.

(21) Appl. No.: 13/021,864

(22) Filed: Feb. 7, 2011

(65) Prior Publication Data

US 2011/0194073 A1  Aug. 11, 2011

(30) Foreign Application Priority Data

Feb. 11, 2010  (DE) .................... 10 2010 001 853

(51) Int. Cl.
*A61B 3/10* (2006.01)
(52) U.S. Cl.
USPC ......................................................... 351/216
(58) Field of Classification Search
USPC ......................................................... 351/216
See application file for complete search history.

(56) References Cited

U.S. PATENT DOCUMENTS

| | | | |
|---|---|---|---|
| 4,856,872 A | 8/1989 | Spitznas et al. | |
| 5,009,487 A | 4/1991 | Reiner | |
| 5,282,085 A | 1/1994 | Volkert et al. | |
| 5,535,060 A | 7/1996 | Grinblat | |
| 6,598,972 B2 | 7/2003 | Strahle | |
| 7,423,807 B2 * | 9/2008 | Sander | 359/381 |
| 7,593,156 B2 * | 9/2009 | Sander | 359/376 |
| 2005/0012994 A1 | 1/2005 | Sander | |
| 2007/0047070 A1 | 3/2007 | Sander | |

FOREIGN PATENT DOCUMENTS

| | | |
|---|---|---|
| DE | 89 02 035 U1 | 3/1989 |
| GB | 2255651 A | 11/1992 |
| WO | 91/15150 A1 | 10/1991 |

OTHER PUBLICATIONS

Oculus Optikgeräte GMBH, "SDI II BIOM II" brochure, Sep. 1998.
HS Möller-Wedel International, "EIBOS for Wide-Angle Fundus Observation" brochure, Jul. 2000, Germany.
Leica Microsystems, "Ophthalmo-logic Retinal Accessories" selling guide, Sep. 2005.
Oculus Optikgeräte GMBH, "Oculus SDI 4 Stereoscopic Diagonal Inverter" brochure, Sep. 2008.
Oculus Optikgeräte GMBH, "Oculus SDI 4 / BIOM 4" brochure, Sep. 2008.

* cited by examiner

*Primary Examiner* — Jack Dinh
(74) *Attorney, Agent, or Firm* — Hodgson Russ LLP

(57) ABSTRACT

Attachment module for a microscope, having an ophthalmoscopic lens (142; 242; 342) and an inverting device (140; 240; 340) for inverting an image of an object (143; 243; 343) that is to be observed generated by means of the ophthalmoscopic lens, wherein the inverter device comprises at least four deflection surfaces (146a, 146b, 146c; 246a, 246b, 246c; 346a, 346b, 346c, 346d) by means of which observation beam paths (102) which emanate from the object to be observed can be introduced into a main objective (110) of the microscope, at least two deflection surfaces being planar and at least two further deflection surfaces being non-planar, particularly spherical or in the shape of free-form surfaces.

21 Claims, 4 Drawing Sheets

ATTACHMENT MODULE FOR A MICROSCOPE FOR OBSERVING THE FUNDUS OF THE EYE

CROSS REFERENCE TO RELATED APPLICATIONS

Figure 1:
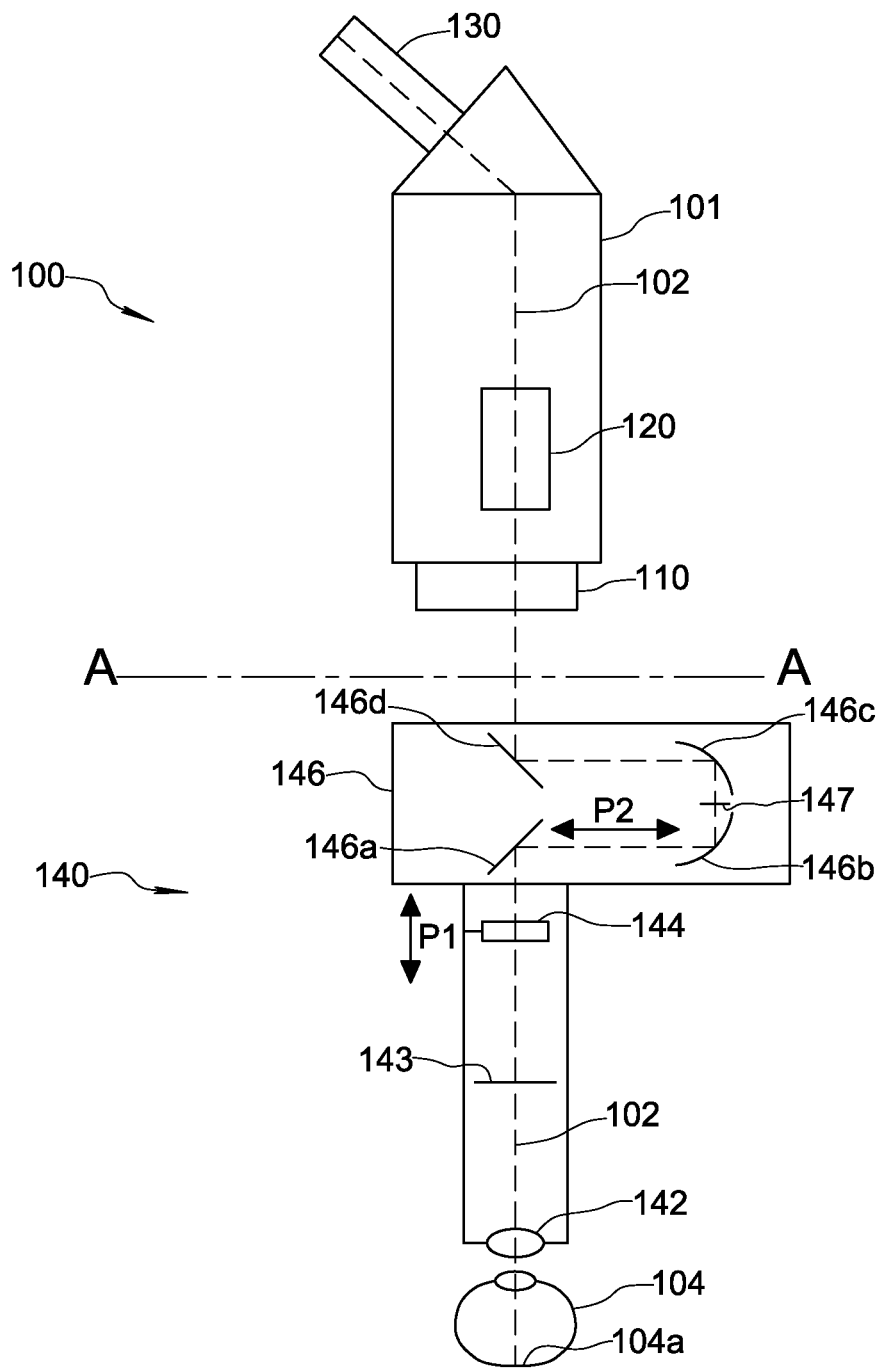

This application claims priority of German patent application number 10 2010 001 853.8 filed Feb. 11, 2010, the entire disclosure of which is incorporated by reference herein.

FIELD OF THE INVENTION

The present invention relates to an attachment module for a microscope having a main objective lens, and to a microscope constructed with a corresponding attachment module, particularly a stereomicroscope.

BACKGROUND OF THE INVENTION

Stereomicroscopes constructed as operating microscopes are described in detail for example in W. H. Lang, F. Muchel. "Zeiss Microscopes for Microsurgery", published by Springer, Berlin, Heidelberg, New York, 1981. Ophthalmological microscopes are also described therein. These have a main objective, a magnification system provided downstream thereof and a binocular tube with eyepieces. In order to produce a stereomicroscope, in a magnification system constructed as a zoom system, for example, the optical path passing through the main objective may be split into a number of optical paths in order for example to enable the object to be viewed simultaneously by a first user (main operator or surgeon) and a second user (assistant).

For intraocular surgery, for example to make it possible to observe the fundus or parts of the vitreous humour close to the fundus of a human eye, additional optical means are required on the stereomicroscopes. These consist of lenses that are provided upstream of the main objective (on the object side).

Additional optical means of this kind are known from the brochure "SDI II, Biom II" by Okulus Optikgeräte GmbH, dating from 1998, and from U.S. Pat. No. 4,856,872. They comprise a lens that is to be arranged close to the object to be observed (ophthalmoscopic lens) and a lens arranged closer to the main objective (reduction lens).

From DE 41 146 46 C2, a solution is known in which an ophthalmological attachment is housed in an attachment housing that can be positioned to the side of the main objective. The attachment comprises an ophthalmoscopic lens, an optical system for image rectification and a movable lens (correcting lens) for focusing.

A system for image rectification is needed as the additional optical means display the microscopic image vertically and laterally reversed (inverted) and hence pseudostereoscopically to the viewer. This means, among other things, that the intermediate image generated by the ophthalmoscopic lens shows the foreground and background reversed in depth perception. However, to be able to perform microsurgery, a rectified image is essential.

Special additional optical means used in eye surgery are so-called wide-angle observation systems which make it possible to look into the interior of the eye, providing a large viewing angle. For this, the ophthalmoscopic lens has to be arranged as close as possible to the eye. Viewing angles of up to about 130° can be achieved, while a distinction is made between contact and non-contact systems depending on whether or not the eye is touched. One unwanted side-effect even with such large observation angles is the fact that the images generated are also diagonally inverted.

Typically, these effects are corrected using a special system of prisms (inverter system). In connection with this, reference may be made by way of example to the EIBOS system of the company Müller-Wedel, which is advantageous in that the inverter is already provided underneath the microscope and delivers the correct image to the microscope. However, this system is regarded as optically relative complicated. In addition it is relative bulky and heavy.

SUMMARY OF THE INVENTION

The present invention endeavors to provide a simplified or small and lightweight attachment module for a microscope with which the particular issues described that occur in intraocular surgery can be compensated.

This problem is solved by an attachment module having the features of claim 1 and a microscope constructed with a corresponding attachment module. By the term attachment module is meant here a module that is arranged between the object to be viewed and a main objective of the microscope.

The solution according to the invention of constructing, within the scope of an attachment module, an inverting device with at least four deflection surfaces, of which at least two are planar and at least two more are non-planar, particularly spherical or in the shape of free-form surfaces, makes it possible to produce an attachment module that is compact and lightweight in construction. The deflection surfaces referred to here are, in particular, components that deflect the observation beam paths impinging on them substantially through 90° The arrangement according to the invention is considerably easier to produce, and also to adjust, than the prior art. It is particularly preferable to use precisely four deflection surfaces, of which two are of planar construction and two more are of non-planar, more particularly spherical construction.

Advantageous embodiments of the invention are recited in the present specification.

According to a preferred embodiment, at least one planar deflection surface is in the form of a plane mirror. Plane mirrors of this kind are easy to adjust and are very small and lightweight in construction.

It is also preferable to construct at least one non-planar deflection surface as a concave mirror. Concave mirrors of this kind also have the same advantages as the plane mirrors mentioned above.

Thus, it is particularly preferable to construct all the deflection surfaces as plane mirrors or concave mirrors.

According to another preferred embodiment, it is envisaged that at least one planar deflection surface is constructed as a planar surface of a glass block, and at least one non-planar deflection surface as a spherical deflection surface of a glass block. The use of glass blocks is characterized by the possibility of a particularly precise and robust positioning in connection with an adjustment. The glass blocks may be arranged so as to enable total reflection to be utilized. On the other hand, the surfaces of the glass blocks that bring about a deflection may also have a mirror finish.

In particular, it is preferable to construct all the deflection surfaces as planar or spherical surfaces of at least one glass block.

It is particularly possible to construct all the deflection surfaces on a single glass block, thus enabling the attachment module to be made very compact in design.

According to another preferred embodiment of the attachment module according to the invention, at least one, and in particular two or all of the deflection surfaces are constructed as optoelectronic elements, particularly micromirror arrays or fluid mirrors. The term fluid mirrors here refers to fluid lenses with a mirrored surface. The term "fluid lens" is explained in more detail hereinafter. This construction allows particularly flexible handling of a microscope constructed with a corresponding attachment module.

Micromirror arrays of this kind may advantageously be used in conjunction with ophthalmoscopic lenses and/or correcting lenses constructed as fluid lenses. A fluid lens is an electrically actuated optical lens of variable focal length. It consists for example of two different liquids with different refractive indices. The focal length of the fluid lens can be varied by means of an electrical field that can be applied from outside. It is thus possible to carry out non-ophthalmological observations with a microscope, for example by setting the focal length to ∞ and setting the micromirror arrays as planar deflection surfaces.

The deflection surfaces are expediently arranged so that observation beam paths emanating from the object are first deflected on a first planar deflection surface, then on a first non-planar or spherical deflection surface, then on a second non-planar or spherical deflection surface and finally on a second planar deflection surface. It is also possible to provide a different sequence of planar and non-planar deflection surfaces.

It has proved particularly advantageous to provide a correcting lens between the ophthalmoscopic lens and the first deflection surface, and/or to make the distance between the first planar and the first spherical deflection surface variable. These measures, on their own or taken together, make it possible to focus on areas of the object that are of particular interest, for example even in the vicinity or region of the fundus of an eye that is under observation.

BRIEF DESCRIPTION OF THE DRAWING VIEWS

Figure 2:
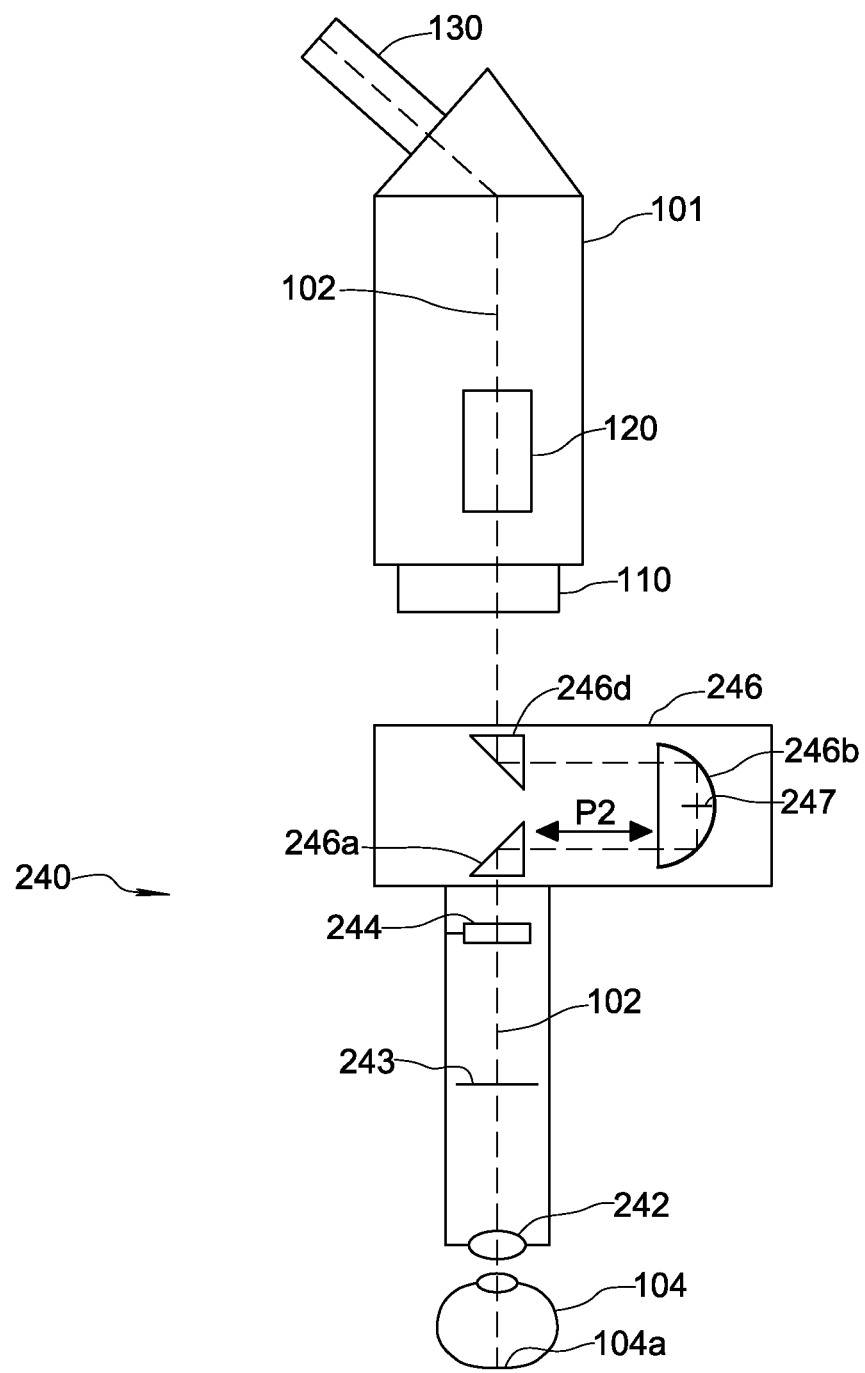
Figure 3:
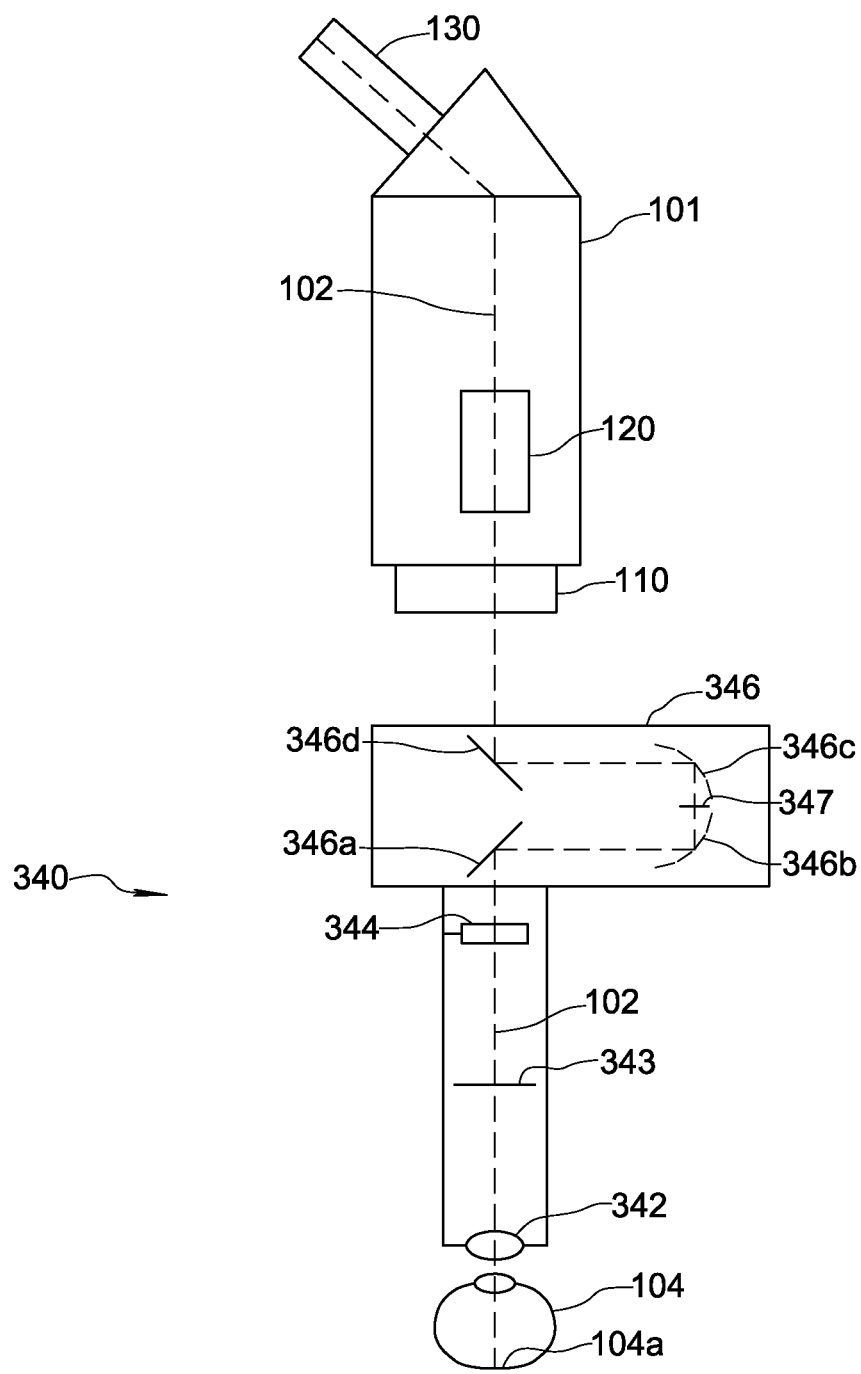
Figure 4:
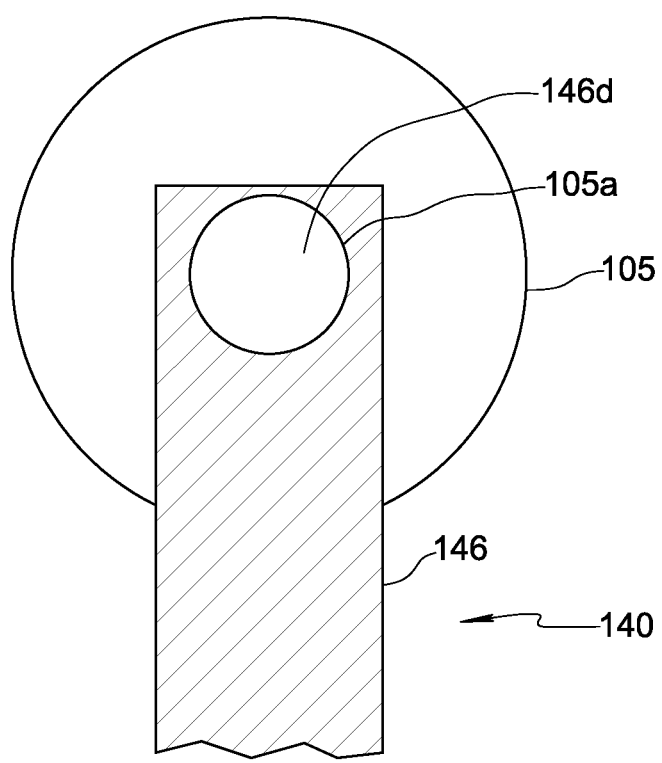

The invention will now be described in more detail with reference to the attached drawings, wherein:

FIG. 1 shows a first preferred embodiment of a microscope with an attachment module according to the invention in schematic sectional side view, FIG. 2 shows an alternative embodiment of a microscope with an attachment module according to the invention in schematic sectional side view, FIG. 3 shows another preferred embodiment of a microscope with an attachment module according to the invention in schematic sectional side view, and FIG. 4 shows a schematically simplified sectional view of the attachment module on the line A-A in FIG. 1.

DETAILED DESCRIPTION OF THE INVENTION

A stereomicroscope is generally designated 100 in FIG. 1. It comprises a housing 101. The microscope 100 is constructed as a stereomicroscope with at least two beam paths, preferably four beam paths (two each for a main operator and two for an assistant). In the Figures only one observation beam path is shown, designated 102, to simplify the drawing.

The microscope has a main objective 110, a zoom system 120 downstream thereof and a binocular tube 130 the eyepieces of which are not shown in detail.

The microscope 100 is also equipped with a first preferred embodiment of the attachment module according to the invention, generally designated 140, which makes it possible to perform intraocular surgery.

The attachment module 140 comprises an ophthalmoscopic lens (fundus lens) 142 and a correcting lens 144. The ophthalmoscopic lens 142 serves to optically compensate the refractive power of the eye 104 that is to be observed.

The attachment module also has an inverter device 146 which comprises four deflection surfaces 146a, 146b, 146c and 146d. These serve to deflect observation beam paths 102 emanating from the 104 into the main objective 110.

The deflection surfaces 146a and 146d are constructed as plane mirrors and the deflection surfaces 146b, 146c are constructed as concave mirrors.

Vertically extending observation beam paths 102 emanating from the eye 104 that is to be observed, after passing through the ophthalmoscopic lens 142 and the correcting lens 144, first strike the planar deflecting mirror 146a, where they are deflected into the horizontal direction. Then they strike the first concave mirror 146b, which deflects them back into the vertical direction. The observation beam paths then strike the second concave mirror 146c, which deflects them back into the horizontal direction once again, after which they strike the second plane mirror 146d which deflects them back into the vertical direction, into the main objective 110.

Regarding the mode of operation of the attachment module 146, it should be mentioned that the ophthalmoscopic lens 142 generates a first intermediate image 143 of the object (fundus 104a of the eye 104). This intermediate image is reversed vertically and laterally (pseudostereoscopically). The correcting lens 144 is expediently movable parallel to the beam path between the ophthalmoscopic lens and vertical correcting lens (indicated by a double arrow P1). The displacement of the correcting lens 144 makes it possible for example to focus on an area of interest on the object or eye 104 without having to make adjustments to the optical systems in the housing 101. When a correcting lens 144 of this kind is used, the spacing between the first (planar) deflecting mirror 146a and the first concave mirror 146b is expediently fixedly preset.

To generate an image which is vertically and laterally true from the intermediate image 143, the deflecting elements 146b, 146c, as already mentioned, are constructed as concave mirrors (non-planar mirrors with a radius of curvature other than ∞). In all, the following propagation of the observation beam paths 102 is obtained: The beam paths resulting from the vertically and laterally reversed intermediate image 143 strike the correcting lens 144. This serves to compensate a change in the optical distance produced by means of the attachment module, in relation to an optical distance which would occur if no attachment module were used between the object and the main objective. Depending on the design and the resulting optical distances, this correcting lens 144 will be constructed as a collimating or scattering lens.

This beam path is deflected into the horizontal by means of the plane mirror 146a. By means of the first concave mirror 146b, another intermediate image 147 is then produced in the vertical beam path between the two concave mirrors 146b, 146c. This intermediate image 147 is laterally and vertically true, i.e. stereoscopic. This intermediate image 147 is then deflected back into the horizontal by means of the second concave mirror 146c. This horizontal beam path is, as already mentioned, deflected into the vertical by the other plane mirror 146d and imaged in the microscope as a paraxial beam path according to ∞ through the main objective 110.

After passing through the main objective 110, the observation beam paths 120 strike the preferably four-channeled zoom system 120, thus providing stereoscopic splitting for a main operator and an assistant.

At this point, the dual functionality of the concave mirrors 146b, 146c should be emphasized. On the one hand, they serve to deflect the beam paths and on the other hand they invert a pseudostereoscopic intermediate image. The provision of concave mirrors of this kind is a simple and inexpensive way of providing image rectification of an inverted pseudostereoscopic intermediate image.

According to an alternative embodiment of the attachment module 140 shown in FIG. 1, the correcting lens 144 may be omitted. In this case, the focusing may be directed to an area of interest on the object or eye 104 by changing the distance between the first planar deflecting mirror 146a and the first concave mirror 146b (illustrated by the double arrow P2). This embodiment is characterized in that only one lens (ophthalmoscopic lens 142) is needed between the eye 104 and the first planar deflecting mirror 146a. It is also possible to provide a correcting lens 144 and at the same time make the distance between the plane mirror 146a and the concave mirror 146b variable.

If a correcting lens 144 is omitted, the curvature (focal length) of the concave mirror 146b should be selected accordingly.

Another possibility is to do away with the correcting lens 144 and to obtain the focusing provided by it using a first deflecting element in the form of a concave mirror instead of the first planar deflecting mirror 146a. This would mean that a total of three of the four deflecting mirrors would be non-planar and one deflecting mirror would be planar in construction.

The particular advantage of the arrangement of the attachment module 140 according to the invention is that a vertically and laterally true image of an object to be observed, for example the retina or the fundus, can easily be provided, but because of the compact construction of the attachment module, which may be constructed so that only some of the light emanating from the object is deflected, the surrounding area, for example the iris and sclera of the patient's eye, can also be observed at the same time. Moreover, the incisions made in the eye for the surgical instruments used in each case can be viewed. The guiding of the instruments can be viewed particularly well. These correlations will now be explained with reference to FIG. 4:

FIG. 4 shows the attachment module 140 in a sectional view on the line A-A, i.e. from above. First of all the field of vision 105 associated with the object or eye 104 (not shown here) will be seen. The inverter device 146 projects into this field of vision 105. At the end of the inverter device 146, which is arranged substantially above the centre of the field of vision 105, it is possible to see the field of vision 105a for the fundus 104a (also not shown) of the eye 104. The mirror 146d through which the corresponding beam paths are introduced into the main objective 110 can be seen in FIG. 4.

Thus, in total, two concentric fields of vision 105, 105a are provided. Because of the compact (narrow) construction of the attachment module 140, particularly the inverter device 146, the area of the outer field of vision 105 that is covered by the inverter device 146 is relatively small. It should be pointed out in this context that the representation of the inverter device 146 in FIG. 4 is purely diagrammatic.

It should also be noted that the additional embodiments of the attachment module according to the invention described hereinafter may be of similarly compact or narrow construction, and thus the same advantageous observation of the inner and outer field of vision can be provided.

An alternative embodiment of the attachment module or microscope according to the invention is shown in FIG. 2. Identical components, which have already been discussed with reference to FIG. 1, have been given the same reference numerals. Here, in an attachment module 240, the planar mirrors or concave mirrors have been replaced by glass blocks formed with corresponding surfaces. The observation beam paths 102 emanating from the eye that is to be observed, in accordance with the beam path propagation shown in FIG. 1, enter the inverter device 246 after passing through the correcting lens, here designated 244.

This inverter device 246 is constructed with glass blocks 246a, 246b, 246d, which are designed so that in their functionality they correspond substantially to the deflecting surfaces 146a to 146d of the first embodiment.

Specifically, the inverter device 246 comprises two glass blocks 246a, 246d, which in the cross-section shown are in the form of right-angled triangles, and another glass block 246b which has one or two spherical curvatures or convexities. In the embodiment shown, the glass block 246b has a spherical curvature or convexity, but it is so dimensioned that two reflections of the observation beam paths 102 can be achieved, as described below:

By means of the ophthalmoscopic lens 242, a first vertically and laterally reversed intermediate image 243 is produced. The correcting lens 244 carries out the conversion into a paraxial beam path. The observation beam paths emanating from the correcting lens 244 first strike a first surface of the glass block 246a, which is arranged perpendicularly to the observation beam paths 102 (extending vertically here), so that they are substantially transmitted from this surface. Then they strike another surface of the glass block 246a, which is arranged at an angle of about 45° to the (vertically extending) observation beam paths 202, so that the latter are deflected through about 90° into the horizontal. The horizontally extending observation beam paths then strike a first planar surface of the glass block 246b, which is arranged perpendicularly to the (horizontally extending) observation beam paths, so that here again transmission takes place. Then the observation beam paths 102 strike the spherically constructed second side of the glass block 246b, where they are deflected through 90°, i.e. back into the vertical. The spherical convexity of the glass block 246b is dimensioned so that the now vertically extending observation beam paths strike the spherical convexity for a second time, to then be deflected once more by the further glass block 246d (analogously to the mode of operation of the glass block 246a) into the vertical and hence into the main objective 110.

In the embodiment according to FIG. 2 it will be seen that the glass blocks are deflected, utilizing the total reflection. It is advantageously possible to provide glass blocks having mirrored deflection surfaces. Glass blocks with mirrored deflection surfaces may have the same spatial orientation as the glass blocks shown in FIG. 2, in which beam paths (emanating from the object) first strike a surface of the respective glass blocks that is oriented perpendicularly to the direction of propagation, and then strike a deflecting surface. However, it is also possible to arrange the glass blocks so that the observation beam paths strike only the mirrored deflection surfaces of the respective glass blocks. It is also possible for example to replace the glass blocks 246a and 246d with a glass block having two correspondingly mirrored deflection surfaces.

The surfaces of the glass blocks from which the observation beam paths are deflected correspond in their functionality to the deflecting mirrors 146a to 146d described with reference to the first embodiment, and therefore reference may be made to these remarks with regard to the inversion produced. It should merely be pointed out that a stereoscopic intermediate image 247 is produced analogously in the vertical beam path between the two deflections on the spherical convexity of the glass block 246*b*.

In the embodiment shown, three glass blocks 246*a*, 246*b* and 246*d* are provided. It is also possible to construct the glass blocks 246*a* and 246*d* as a unified glass block, for example. It is also possible to construct all three glass blocks 246*a*, 246*b* and 246*d* as a unified glass block.

If the glass blocks 246*a*, 246*b* and 246*d* are constructed as different glass blocks, or if at least the glass block 246*b* is constructed as an individual glass block, it is once again possible to dispense with the correcting lens 244 if the spacing between the first glass block 246*a* and the second glass block 246*b* is made variable. It is also possible to construct the first glass block 246*c* with a focusing facility, i.e. to give it a corresponding spherical convexity in order to replace the correcting lens 244 wholly or partially. Reference may be made to the corresponding remarks concerning the first embodiment.

Another embodiment of the attachment module or microscope according to the invention is shown in FIG. 3. Components identical to those already shown in FIG. 1 or 2 have been given the same reference numerals.

It will be seen here that in an attachment module 340 the concave mirrors of the first embodiment or the spherical convexities of the glass blocks according to the second embodiment have been replaced by respective optoelectronic elements (schematically shown) such as e.g. micromirror arrays 346*b*, 346*c*. The corresponding arrangement of the micromirrors is a simple way of achieving the functionality of a concave mirror or of a spherical convexity of a glass block, so that all in all an intermediate image 343 which is vertically and laterally reversed can be inverted into a correctly stereoscopic image 347.

This embodiment is characterized in that by suitable control micromirror arrays of this kind can also be arranged so as to provide a planar functionality. This switchability means that a correspondingly equipped microscope is more flexible in use without the need for mechanically moving parts.

In this context it has proved favorable to construct the ophthalmoscopic lens, here designated 342, and/or the correcting lens, here designated 344, as controllable fluid lenses which can be switched to a focal length of ∞ if necessary. If such a fluid lens and micromirror arrays 346*b*, 346*c* with planar functionality are used simultaneously, the microscope can readily also be used for non-ophthalmoscopic applications. One aspect that has proved particularly advantageous is that the attachment module 340, in contrast to the prior art, does not have to be pivoted out of the observation beam path, but instead can remain at the location shown. There is absolutely no need here for corresponding adjustment and pivoting mechanisms, which were required in the prior art as a result of the provision of a microscope with ophthalmological and non-ophthalmological functionality. It is also possible for example to replace the micromirror arrays 346*b*, 346*c* with mirrored fluid lenses which may assume the form of a scattering lens when subjected to a corresponding application of electricity. The combination of the form of a scattering lens with a mirrored surface performs the same functionality as a concave mirror.

The system is designed for at least two stereoscopic beam paths for a main operator. However, it is preferably designed for four stereoscopic beam paths to accommodate an assistant as well.

List of Reference Numerals
- 100 stereomicroscope
- 101 housing
- 102 observation beam path
- 104 eye
- 104*a* retina
- 105,105*a* field of vision
- 110 main objective
- 120 zoom system
- 130 binocular tube
- 140,240,340 attachment module
- 142,242,342 ophthalmoscopic lens (fundus lens)
- 143,243,343 intermediate image
- 144,244,344 correcting lens
- 146 inverter device
- 146*a*, 146*b*, 146*c*, 146*d* deflection surfaces/deflecting mirrors
- 147,247,347 intermediate image
- 244 correcting lens
- 246 inverter device
- 246*a*,246*b*,246*d* glass blocks
- 342 ophthalmoscopic lens
- 346*b*, 346*c* micromirror array

What is claimed is:

1. An attachment module for use with a microscope having a main objective, the attachment module comprising:
    an ophthalmoscopic lens arranged to generating an image of an object to be observed; and
    an inverter device for inverting the image generated by the ophthalmoscopic lens;
    wherein the inverter device includes at least four deflection surfaces by which observation beam paths emanating from the object to be observed are introduced into the main objective of the microscope, at least two of said deflection surfaces being planar and at least two further ones of said deflection surfaces being non-planar;
    wherein the attachment module is configured to be arranged between the object to be observed and the main objective of the microscope.

2. The attachment module according to claim 1, wherein the non-planar deflection surfaces are spherical deflection surfaces.

3. The attachment module according to claim 1, wherein the non-planar deflection surfaces are in the shape of freeform surfaces.

4. The attachment module according to claim 1, wherein at least one of the planar deflection surfaces is a plane mirror.

5. The attachment module according to claim 1, wherein at least one of the non-planar deflection surfaces is a concave mirror.

6. The attachment module according to claim 1, wherein all of the deflection surfaces are selected from the group consisting of plane mirrors and concave mirrors.

7. The attachment module according to claim 1, wherein at least one of the planar deflection surfaces is a planar surface of a glass block and at least one of the non-planar deflection surfaces is a spherical deflection surface of another glass block.

8. The attachment module according to claim 1, wherein all of the deflection surfaces are surfaces of at least one glass block.

9. The attachment module according to claim 8, wherein the at least one glass block is exactly one single glass block, and all of the deflection surfaces are surfaces of the single glass block.

10. The attachment module according to claim 1, wherein at least one of the deflection surfaces is formed by an optoelectronic element.

11. The attachment module according to claim 10, wherein the optoelectronic element is a micromirror array.

12. The attachment module according to claim 10, wherein the optoelectronic element is a fluid mirror.

13. The attachment module according to claim 10, wherein at least two of the deflection surfaces are formed by optoelectronic elements.

14. The attachment module according to claim 13, wherein all of the deflection surfaces are formed by optoelectronic elements.

15. The attachment module according to claim 1, wherein the deflection surfaces are arranged so that the observation beam paths emanating from the object are first deflected by a first deflection surface, then deflected by a second deflection surface, then deflected by a third deflection surface, and finally deflected by a fourth deflection surface.

16. The attachment module according to claim 15, wherein the first deflection surface and the fourth deflection surface are planar deflection surfaces, and the second deflection surface and the third deflection surface are spherical deflection surfaces.

17. The attachment module according to claim 15, further comprising a correcting lens between the ophthalmoscopic lens and the first deflection surface.

18. The attachment module according to claim 17, wherein the correcting lens is a fluid lens.

19. The attachment module according to claim 15, wherein a distance between the first deflection surface and the second deflection surface is variable.

20. The attachment module according to claim 1, wherein the ophthalmoscopic lens is a fluid lens.

21. A stereomicroscope comprising:
a main objective; and
an attachment module, the attachment module comprising:
    an ophthalmoscopic lens arranged to generating an image of an object to be observed; and
    an inverter device for inverting the image generated by the ophthalmoscopic lens, wherein the inverter device includes at least four deflection surfaces by which observation beam paths emanating from the object to be observed are introduced into the main objective, at least two of said deflection surfaces being planar and at least two further ones of said deflection surfaces being non-planar;
wherein the attachment module is configured to be arranged between the object to be observed and the main objective of the microscope.

* * * * *